US010492562B2

(12) United States Patent
Boeck et al.

(10) Patent No.: US 10,492,562 B2
(45) Date of Patent: Dec. 3, 2019

(54) WORK SHOE

(71) Applicant: Robert Bosch GmbH, Stuttgart (DE)

(72) Inventors: Cornelius Boeck, Kirchheim (DE);
Daniel Barth, Leinfelden-Echterdingen (DE); Joachim Schadow, Stuttgart (DE); Joerg Maute, Sindelfingen (DE); Joern Stock, Bempflingen (DE); Florian Esenwein, Leinfelden-Echterdingen (DE); Manfred Lutz, Filderstadt (DE)

(73) Assignee: Robert Bosch GmbH, Stuttgart (DE)

( * ) Notice: Subject to any disclaimer, the term of this patent is extended or adjusted under 35 U.S.C. 154(b) by 291 days.

(21) Appl. No.: 15/322,390

(22) PCT Filed: Apr. 2, 2015

(86) PCT No.: PCT/EP2015/057304
§ 371 (c)(1),
(2) Date: Dec. 27, 2016

(87) PCT Pub. No.: WO2016/000838
PCT Pub. Date: Jan. 7, 2016

(65) Prior Publication Data
US 2017/0127749 A1    May 11, 2017

(30) Foreign Application Priority Data

Jun. 30, 2014   (DE) .................. 10 2014 212 535

(51) Int. Cl.
*A43B 3/00*   (2006.01)
*A43B 3/24*   (2006.01)
(Continued)

(52) U.S. Cl.
CPC ............ *A43B 3/001* (2013.01); *A43B 3/0005* (2013.01); *A43B 3/246* (2013.01); *A43B 7/32* (2013.01);
(Continued)

(58) Field of Classification Search
None
See application file for complete search history.

(56) References Cited

U.S. PATENT DOCUMENTS 7,579,946 B2 *  8/2009  Case, Jr. ............... A43B 3/0005
                                                         340/539.1
7,724,132 B1    5/2010  Daniel
(Continued)

FOREIGN PATENT DOCUMENTS

JP      5-228002 A      9/1993
JP      3120749 U       4/2006
(Continued)

OTHER PUBLICATIONS

English language abstract of CN103271492B; Oct. 7, 2015 (Year: 2015).*
(Continued)

*Primary Examiner* — Robert K Carpenter
(74) *Attorney, Agent, or Firm* — Maginot, Moore & Beck LLP

(57) ABSTRACT

A work shoe, in particular a safety shoe, includes at least one passive protection unit which is intended to passively protect a shoe wearer at least against mechanical and/or electrical loads, and includes at least one active protection unit which has at least one sensor unit which is intended to detect at least one characteristic variable at least in order to enable a protection function and/or a comfort function. The sensor unit is configured at least for detecting at least one person-
(Continued)

related characteristic variable and/or at least one environmental characteristic variable.

18 Claims, 3 Drawing Sheets

(51) Int. Cl.

| | | |
|---|---|---|
| A43B 7/36 | (2006.01) | |
| A43B 23/08 | (2006.01) | |
| G08B 5/36 | (2006.01) | |
| G08B 25/01 | (2006.01) | |
| G08B 5/02 | (2006.01) | |
| A43B 7/32 | (2006.01) | |
| A61B 5/01 | (2006.01) | |
| A61B 5/103 | (2006.01) | |
| A61B 5/00 | (2006.01) | |
| A43B 13/02 | (2006.01) | |
| G05B 15/02 | (2006.01) | |
| A61B 5/11 | (2006.01) | |

(52) U.S. Cl.
CPC .............. *A43B 7/36* (2013.01); *A43B 13/026* (2013.01); *A43B 23/082* (2013.01); *A43B 23/087* (2013.01); *A61B 5/0002* (2013.01); *A61B 5/01* (2013.01); *A61B 5/1036* (2013.01); *A61B 5/1038* (2013.01); *A61B 5/6807* (2013.01); *G05B 15/02* (2013.01); *G08B 5/36* (2013.01); *G08B 25/016* (2013.01); *A61B 5/1112* (2013.01); *A61B 5/1117* (2013.01); *A61B 2503/20* (2013.01); *A61B 2560/0242* (2013.01)

(56) References Cited

U.S. PATENT DOCUMENTS

| | | |
|---|---|---|
| 2013/0041617 A1 | 2/2013 | Pease et al. |
| 2014/0118498 A1* | 5/2014 | Lee ................... A43B 3/0005 348/46 |

FOREIGN PATENT DOCUMENTS

| | | |
|---|---|---|
| JP | 2007-260091 A | 10/2007 |
| JP | 2009-11460 A | 1/2009 |
| JP | 2010-201069 A | 9/2010 |
| JP | 2013-536040 A | 9/2013 |
| KR | 2002-0061662 A | 7/2002 |

OTHER PUBLICATIONS

International Search Report corresponding to PCT Application No. PCT/EP2015/057304, dated Jul. 9, 2015 (German and English language document) (8 pages).

* cited by examiner

WORK SHOE

This application is a 35 U.S.C. § 371 National Stage Application of PCT/EP2015/057304, filed on Apr. 2, 2015, which claims the benefit of priority to Serial No. DE 10 2014 212 535.9, filed on Jun. 30, 2014 in Germany, the disclosures of which are incorporated herein by reference in their entirety.

BACKGROUND

Document KR 2002 0061662 A1 already makes known a work shoe, in particular a safety shoe, having a passive protective unit which is provided for passively protecting a shoe wearer at least against mechanical and/or electrical loads, and having an active protective unit which has a sensor unit which is provided for detecting a characteristic variable at least in order to enable a protective function and/or a comfort function. In this case, the sensor unit is provided for detecting a load characteristic variable of a safety toecap element of the work shoe in order to enable an overload protection function.

SUMMARY

The disclosure is directed to a work shoe, in particular a safety shoe, having at least one passive protective unit which is provided for passively protecting a shoe wearer at least against mechanical and/or electrical loads, and having at least one active protective unit which has at least one sensor unit which is provided for detecting at least one characteristic variable at least in order to enable a protective function and/or a comfort function.

It is proposed that the sensor unit is provided at least for detecting at least one person-related characteristic variable and/or at least one environmental characteristic variable. In this case, a "person-related characteristic variable" is intended to be understood to mean, in particular, a characteristic variable which defines at least one vital value of a shoe wearer of the work shoe and/or which is dependent on a behavior of a shoe wearer of the work shoe, such as, for example, a direction and/or a location of a force effect of a shoe wearer onto the work shoe. The person-related characteristic variable can be designed, in this case, as a user-specific work shoe load type, in particular a sole load type of the work shoe, as a support load, such as, for example, a noise impact and/or a vibration load, as a pulse of a shoe wearer of the work shoe, as a body temperature of a shoe wearer of the work shoe, as a tiredness characteristic variable of a shoe wearer of the work shoe, as a support orientation characteristic variable, as a shoe movement characteristic variable, or as another person-related characteristic variable which appears reasonable to a person skilled in the art. In this case, an "environmental characteristic variable" is intended to be understood to mean, in particular, a characteristic variable which defines an environment surrounding the work shoe. In this case, the environmental characteristic variable can be in the form of ambient pressure, ambient temperature, ambient noise level, an ambient gas characteristic variable, an ambient voltage characteristic variable, an ambient humidity characteristic variable, an ambient acid and/or ambient base characteristic variable, or as another environmental characteristic variable which appears reasonable to a person skilled in the art.

In this case, the term "safety shoe" is intended to define a type of shoe, in particular, which satisfies at least one criterion of the criteria mentioned in EN ISO 20345. Therefore, the passive protective unit includes at least one safety toecap element and/or at least one anti-penetration element. In this case, the safety toecap element can be made from steel or from a plastic.

Preferably, the safety toecap element has, in particular, a protective effect against an impact energy of at least 200 J and a protective effect against a pressure load of at least 15 kN. The anti-penetration element can be made from steel or from a woven fabric structure, such as, for example, a Kevlar structure. Preferably, the anti-penetration element is designed as a layer, in particular as an intermediate layer, of a sole of the work shoe. Preferably, the sole of the work shoe is designed to be oil- and/or fuel-resistant, electrically insulating, and/or heat-resistant. The work shoe can also have further characteristics which appear reasonable to a person skilled in the art and which are mentioned in EN ISO 20345 in respect of a safety shoe. Particularly preferably, the passive protective unit is designed to be free from a power supply. Therefore, the passive safety unit is preferably provided for protecting a shoe wearer of the work shoe via a material property or a geometric characteristic of protective elements of the passive safety unit. "Provided" is intended to be understood to mean, in particular, specially designed and/or specially equipped. The wording that an element and/or a unit is provided for a certain function is intended to be understood to mean, in particular, that the element and/or the unit satisfy/satisfies and/or carry out/carries out this certain function in at least one application state and/or operating state.

By means of the embodiment of the work shoe according to the disclosure, dangerous situations can be advantageously detected and a shoe wearer of the work shoe can be advantageously protected against dangers. In addition, a high level of wearing comfort can be advantageously achieved by way of at least one comfort function being monitored and/or adapted on the basis of sensor data. Therefore, a work shoe can be particularly advantageously provided, which can provide a high level of wearing safety and/or wearing comfort.

In addition, it is provided that the sensor unit includes at least one acceleration sensor element which is provided for detecting at least one acceleration characteristic variable which can be utilized at least for evaluating a safe state of a shoe wearer. In this case, the acceleration sensor element can be designed as a multidirectional acceleration sensor element, in particular as a three-directional acceleration sensor element, as a rotation rate sensor element, as a piezoelectric acceleration sensor element, as an acceleration sensor element made from a microelectromechanical system (MEMS), or as another acceleration sensor element which appears reasonable to a person skilled in the art. By means of the embodiment according to the disclosure, a person-related characteristic variable can be advantageously and cost-effectively ascertained, which variable preferably allows for conclusions to be drawn regarding a safe state of a shoe wearer. In this way, an acceleration characteristic variable induced by a muscular twitching of a shoe wearer, such as, for example, due to an exertion of a muscle when standing on the tips of the toes or the like, can be detected, which variable can be utilized for evaluating a safe state of a shoe wearer. In the case of an exertion of a muscle, a muscular twitching, for example, in a frequency range from 2 to 12 Hz or higher is possible, which can be advantageously utilized for evaluating a safe state of a shoe wearer. Preferably, the acceleration sensor element is advantageously situated, for this purpose, on an inner region of the work shoe facing a shoe wearer. In addition, an acceleration characteristic variable detected by means of the acceleration sensor element can be advantageously utilized for evaluating a presence of a free fall of a shoe wearer, for example, from a ladder, or for evaluating a slipping of a shoe wearer on a slippery underlying surface. Furthermore, an acceleration characteristic variable detected by means of the acceleration sensor element can be advantageously utilized for detecting whether a shoe wearer is in a dangerous situation, in particular when the acceleration sensor element detects no movement and a shoe wearer does not change position for a certain period of time, in particular being in an at least essentially horizontal position relative to an underlying surface.

Advantageously, the sensor unit includes at least one temperature sensor element which is provided for detecting at least one temperature characteristic variable, in particular a body temperature of a shoe wearer, an underlying-surface temperature and/or an ambient temperature. Preferably, the sensor unit therefore includes at least one temperature sensor element which is designed as a body temperature sensor element and which is provided for detecting a body temperature of a shoe wearer of the work shoe. In this case, the temperature sensor element designed as a body temperature sensor element is preferably situated on an inner region of the work shoe. Furthermore, the sensor unit preferably includes at least one temperature sensor element which is designed as an underlying-surface temperature sensor element and which is provided for detecting an underlying-surface temperature of an underlying surface on which the work shoe is situated and/or moved. In this case, the temperature sensor element designed as an underlying-surface temperature sensor element is preferably situated on the sole, in particular in the region of an underlying-surface contact area of the sole. In addition, the sensor unit therefore preferably includes at least one temperature sensor element which is designed as an ambient temperature sensor element and which is provided for detecting an ambient temperature, in particular an ambient air temperature. In this case, the temperature sensor element designed as an ambient temperature sensor element is preferably situated on an outer region of the work shoe. In this case, the temperature sensor element can be integrated directly into an upper material of the work shoe, in particular directly in a material of the upper material, such as, for example, directly in fibers of an upper material. By means of the embodiment according to the disclosure, a temperature characteristic variable can therefore be advantageously detected, which be utilized for an evaluation in respect of a physical state of a shoe wearer of the work shoe, in respect of a comfort function activation, such as, for example, an activation of heating or cooling, and/or in respect of a state of an underlying surface, such as, for example, a risk of ice formation. In this case, it is conceivable that the protective element, which is designed as an anti-penetration element, is designed as a heat conducting element on which, for example, a heating element and/or a cooling element of the work shoe is situated, and the protective element designed as an anti-penetration element provides for good thermal conduction due to a design made from a metallic material. It is also conceivable that, in one embodiment of the protective element designed as an anti-penetration element made from a conductive plastic, the protective element designed as an anti-penetration element itself can be designed as a heating element, for example, by an application of a voltage. By means of the embodiment according to the disclosure, highly diverse temperatures can be advantageously detected in order to provide for high wearer safety.

Furthermore, it is provided that the sensor unit includes at least one pressure sensor element which is provided for detecting at least one pressure characteristic variable, in particular a sole-pressure characteristic variable acting onto a sole by a shoe wearer of the work shoe. In this case, it is conceivable that the sensor unit includes only one single pressure sensor element which is disposed on the sole of the work shoe, or the sensor unit comprises a plurality of pressure sensor elements which are disposed so as to be distributed on the sole and form a single pressure sensor region or multiple pressure sensor regions. Particularly preferably, the sensor unit comprises a plurality of pressure sensor elements which are situated on the sole in a type of grid. In this case, it is conceivable that the pressure sensor element or the pressure sensor elements is/are disposed on a side of the anti-penetration element facing away from an underlying-surface contact area of the sole. Furthermore, it is conceivable that the pressure sensor element or the pressure sensor elements is/are disposed between two anti-penetration elements of the passive protective element. In addition, it is conceivable that the pressure sensor elements situated in a type of grid are disposed in a support element, such as, for example, a woven fabric of the active protective unit and can be inserted, as a pressure sensor element unit, into the work shoe, in particular in a footbed region of the work shoe. It is therefore conceivable that the pressure sensor element unit forms a shoe insert. By means of the embodiment according to the disclosure, a pressure load of a shoe wearer on the work shoe can be advantageously precisely detected. In particular as a result of a distribution of a plurality of pressure sensor elements, a precise detection of a point which is acted upon can be advantageously achieved and can be utilized for evaluating a protective function of the detected pressure characteristic variable.

In addition, it is provided that the work shoe includes at least one evaluation unit which is at least provided for evaluating the detected acceleration characteristic variable in order to detect a safe state of a shoe wearer and/or for evaluating the detected pressure characteristic variable in order to detect a sole load distribution. In this case, a "sole load distribution" is intended to be understood to mean, in particular, a distribution of a force, in particular a compressive force, acting on the work shoe, in particular on the sole, by a shoe wearer of the work shoe. In this case, it is conceivable that the evaluation unit is provided for evaluating characteristic variables from a pair of work shoes or from a single work shoe, wherein, for example, communication can take place between evaluation units of the individual work shoes of a pair of work shoes. By means of the embodiment according to the disclosure, an evaluation in respect of a standing safety of a shoe wearer of the work shoe can be advantageously achieved. Advantageously, an evaluation can be achieved, by means of which it is possible to deduce, for example, that a shoe wearer is kneeling, or is standing on a ladder, that the sole is resting via the entire surface thereof against an underlying surface, that the shoe wearer is standing on the tips of his toes, etc.

In addition, it is provided that the sensor unit comprises at least one location-determining sensor element which is provided for detecting at least one position characteristic variable, in particular at least one global position characteristic variable and/or at least one relative work-area position characteristic variable. For this purpose, the sensor unit preferably includes at least one sensor element which is designed as a GPS sensor element and by means of which a global position of the work shoe can be detected. It is also conceivable, however, that the sensor unit comprises another sensor element which appears reasonable to a person skilled in the art for detecting a position characteristic variable in the form of a global position, such as, for example, a compass position-determining sensor element, a Galileo position-determining sensor element, a GLONASS position-determining sensor element, a Beidou position-determining sensor element, or the like. In addition, the sensor unit preferably comprises at least one sensor element designed as a work-area position-determining sensor element which is provided for enabling a relative position detection of the work shoe within a work area, for example, by means of a travel-time measurement via a WLAN network or a mobile network. Therefore, a detection of a position of the work shoe can be advantageously achieved, which allows for a reliable determination of the location of the work shoe and, therefore, of a shoe wearer of the work shoe, in the case of an emergency, for example. In this case, it is conceivable that a detection of at least one position characteristic variable takes place only if a dangerous situation is detected. Therefore, it is conceivable that a detection of at least one position characteristic variable is deactivated during a non-presence of a dangerous situation is detected.

It is further provided that the work shoe includes at least one communication unit which is provided for communicating with at least one external unit in order to exchange electronic data. The communication unit is preferably designed as a wireless communication unit. In this case, the communication unit can be designed as a WLAN communication unit, a Bluetooth communication unit, a radio communication unit, an RFID communication unit, an NFC communication unit, an infrared communication unit, a mobile network communication unit, as a Zigbee communication unit, or the like. Particularly preferably, the communication unit is provided for bidirectional data transmission. In one alternative embodiment, the communication unit is designed as a cable-bound communication unit, such as, for example, a LAN communication unit, a USB communication unit, a power-line communication unit, a CAN bus communication unit, an Ethernet communication unit, a twisted pair cable communication unit (CAT5 or CAT6), or the like. It is also conceivable, however, that the communication unit is provided as an alternative to a wireless or a cable-bound communication for wireless or cable-bound communication with an external unit. The external unit can be designed as a smartphone, a personal computer, a laptop, a netbook, a tablet, a corporate mainframe computer, a portable machine tool, an output unit, such as, for example, a loudspeaker, work clothing, safety glasses, a safety helmet, or as another external unit which appears reasonable to a person skilled in the art. In an embodiment as a smartphone, a personal computer, a laptop, a netbook, or a tablet, preferably an app is provided for communication with the communication unit. It is also conceivable, however, that the external unit is designed as an external, transportable control unit, as a fixedly installed control unit at a workstation of an operator, as a synchronization unit of a usage location, which unit is fixedly installed in a room and can be controlled from a central office in respect of, for example, company requirements/safety regulations, as a body-characteristic variable monitoring unit, or as a further centralized or decentralized control unit, input station and/or centralized or decentralized terminal which appears reasonable to a person skilled in the art. Advantageously, a synchronization of electronic data can therefore be made possible. If a presence of a shoe wearer of the work shoe, in particular a wearing of the work shoe is detected, for example, by means of a sensor element of the sensor unit, a connection between the communication unit and the external unit is at least partially automatically established. Settings stored in the external unit are therefore preferably directly transferable to the work shoe and/or from the work shoe to the external unit. These can be individualized settings of a shoe wearer or they can be company requirements. In addition, for example, a noise impact of a shoe wearer for the purpose of monitoring compliance with a load limit and/or a possible payment of additional pay to a head office, or the like, can be transmitted by means of the communication unit. By means of the embodiment according to the disclosure, a comfortable, in particular centralized setting of characteristic variables can advantageously take place. In addition, one-man monitoring can be advantageously enabled, so that a head office, advantageously, can remain informed about a state of a shoe wearer of the work shoe and, in particular, about any dangerous situations which may arise. Therefore, a high level of safety for a shoe wearer of the work shoe can be advantageously ensured.

In addition, it is provided that the work shoe includes at least one control and/or regulating unit which is provided for adapting at least one work shoe parameter, in particular a work shoe comfort parameter and/or a work shoe safety parameter, depending on the at least one detected, person-related characteristic variable and/or on the at least one detected environmental characteristic variable. In this case, it is conceivable that the sensor unit includes at least one sensor element which is provided for detecting a closure-force characteristic variable of the work shoe. In addition, the active protective unit could include at least one actuator element which is provided for adapting the closure-force characteristic variable—as a result of a data transmission between the control and/or regulating unit and the actuator element—depending on the at least one detected, person-related characteristic variable and/or on the at least one detected environmental characteristic variable. Furthermore, it is also conceivable that the sensor unit includes at least one underlying-surface condition sensor element which is provided for detecting an underlying-surface condition. In addition, the active sensor unit could include at least one actuator element which is provided for adapting a sole property, such as, for example, soft, hard, with studs, without studs, etc., of the sole of the work shoe—as a result of a data transmission between the control and/or regulating unit and the actuator element—depending on the at least one detected, person-related characteristic variable and/or on the at least one detected environmental characteristic variable. It is also conceivable that the control and/or regulation adapts an active cooling or an active heating of the work shoe depending on the at least one detected, person-related characteristic variable and/or the at least one detected environmental characteristic variable. Further adaptations of work shoe comfort parameters and/or work shoe safety parameters which appear reasonable to a person skilled in the art are also conceivable. By means of the embodiment according to the disclosure, a high level of safety and a high level of comfort of a shoe wearer of the work shoe can be advantageously achieved.

In addition, it is provided that the control and/or regulating unit is provided for accessing—by means of the communication unit—a central database, in which at least one safety and/or operating-area rule are/is stored, which can be utilized at least for adapting at least one work shoe parameter, in particular a work shoe comfort parameter and/or a work shoe safety parameter, and/or for outputting safety information by means of an output unit. Preferably, the control and/or regulating unit automatically evaluates the safety and/or operating-area rules stored in the central database and automatically interprets the safety and/or operating-area rules in order to adapt the at least one work shoe parameter. In this case, it is feasible that the work shoe additionally comprises a control unit, by means of which an adaptation of a work shoe parameter can be manually adjusted by a shoe wearer of the work shoe in order to enable, for example, an individualized setting of the safety and/or operating-area rules. Particularly preferably, in addition to accessing the central data base by means of the communication unit, it is also possible to exchange electronic data with at least one external unit by means of the communication unit. Therefore, a data exchange can preferably take place between the work shoe and further external units, such as, for example, a data exchange between the work shoe and a sensor unit of a piece of work clothing, such as, for example, a safety helmet, a glove, a safety jacket, a pair of safety pants, etc., a smartphone, a laptop, a PC, a cellular phone, a tablet, a server, or the like. In this case, the characteristic variables, in particular the characteristic variables detected by means of the sensor unit of the active protective device and/or the data transmitted by means of the communication unit are preferably exchangeable and/or can be used for adapting the at least one work shoe parameter. Preferably, an external unit, in particular a smartphone, is designed as a router which is provided as the switching center at least between the communication unit and the central database and/or a further unit. In this case, it is advantageous to use an individually matched smartphone. In addition, a check can be carried out by means of the control and/or regulating unit, via the communication unit and due to a connection to a network, such as, for example, a company network, an Internet network, or the like, to determine whether safety settings and/or current climate data (weather) are stored for a position characteristic variable in the form of a global position. By means of the embodiment according to the disclosure, an at least partially automatic accounting for safety and/or operating-area rules can be advantageously utilized in order to adapt the at least one work shoe parameter. Therefore, a high level of wearing comfort and a reliable retention of safety functions can be advantageously ensured.

Furthermore, it is provided that the sensor unit is at least partially situated in or on a passive protective element of the passive protective unit. Preferably, at least one sensor element of the sensor unit is situated at least partially in the safety toecap element. Therefore, at least one passive protective element of the passive protective unit, in or on which the sensor unit is situated, is preferably designed as the safety toecap element. Furthermore, at least one sensor element of the sensor unit is situated at least partially in the anti-penetration element. Therefore, at least one passive protective element of the passive protective unit, in or on which the sensor unit is situated, is preferably designed as the anti-penetration element. A high level of protection of the sensor unit against damage, in particular against damage to sensor elements of the sensor unit, can be advantageously achieved.

In addition, it is provided that the work shoe includes at least one power supply unit and/or one energy accumulator unit which are/is provided at least in order to supply power to the active protective unit. Preferably, the energy accumulator unit is designed as a rechargeable battery unit. The rechargeable battery unit is preferably rechargeable by means of at least one charging interface of the work shoe. In this case, the charging interface can be designed as an inductive charging interface. It is also feasible, however, that the charging interface is designed as a cable-bound charging interface. The power supply unit is preferably designed as a converting power supply unit which is provided for converting mechanical energy into electrical energy. In this case, the power supply unit is preferably designed as a piezo energy supply unit. Therefore, the energy accumulator unit is preferably connected to the power supply unit by means of the charging interface. By means of the embodiment according to the disclosure, autonomously operable safety functions of the work shoe can be advantageously achieved.

In addition, it is provided that the work shoe includes at least one output unit for outputting information at least depending on the at least one detected person-related characteristic variable and/or on the at least one detected environmental characteristic variable and/or depending on information transmitted by means of a communication unit. The output unit in this case can be designed as a haptic, acoustic and/or optical output unit. Preferably, the output unit includes at least one output element which is situated on the work shoe and is provided for outputting a piece of information. The output unit can be controlled and/or regulated preferably by means of the control and/or regulating unit. By means of the embodiment according to the disclosure, a piece of information can be advantageously displayed to a shoe wearer of the work shoe. Therefore, a shoe wearer of the work shoe can be warned, advantageously, about a dangerous situation. In addition, other persons who are situated in the surroundings of the shoe wearer of the work shoe can be likewise advantageously warned about a dangerous situation.

Furthermore, it is provided that the work shoe includes at least one lighting unit for illuminating a work area. Particularly preferably, the lighting unit is situated in a toe region of the work shoe in order to illuminate a work area located in front of the work shoe. It is also conceivable, however, that the lighting unit is situated, alternatively or additionally, in an ankle region of the work shoe in order to illuminate a work area located in front of, next to, and/or behind the work shoe. Particularly preferably, the lighting unit is designed as an LED lighting unit. It is also conceivable, however, that the lighting unit is embodied in another way which appears reasonable to a person skilled in the art, such as, for example, being embodied as a noble gas lighting unit, a laser light lighting unit, or the like. By means of the embodiment according to the disclosure, a high level of safety of a shoe wearer can be advantageously achieved. Advantageously, working safely in dark or poorly lit work areas can be made possible. Therefore, good visibility of a work area can be advantageously achieved.

In addition, it is provided that the work shoe includes at least one projection unit which is provided for projecting at least one piece of information onto an underlying surface. Particularly preferably, the projection unit is situated in a toe region of the work shoe in order to project a piece of information onto an underlying surface in front of the work shoe. It is also conceivable, however, that the projection unit is situated, alternatively or additionally, in an ankle region of the work shoe in order to project a piece of information onto an underlying surface in front of, next to, and/or behind the work shoe. By means of the embodiment according to the disclosure, a reliable legibility of information can be advantageously made possible. In addition, a large area can be used for displaying information.

In addition, a safety system comprising at least one work shoe according to the disclosure and comprising at least one external unit is provided, with which the work shoe communicates at least by means of at least one communication unit of the work shoe in order to exchange electronic data. Therefore, a high level of safety can be advantageously ensured.

Furthermore, it is provided that the at least one external unit is designed as a portable machine tool. In this case, a "portable machine tool" is intended to be understood to mean, in particular, a machine tool for machining workpieces which can be transported by an operator without the aid of a transport machine. The portable machine tool has a mass, in particular, which is less than 40 kg, preferably less than 10 kg, and particularly preferably less than 5 kg. In this case, safety functions of the portable machine tool and/or safety functions of machine tool, which can be situated on the portable machine tool, can be controlled and/or regulated preferably on the basis of the at least one person-related characteristic variable and/or on the basis of the at least one characteristic variable, preferably by means of the control and/or regulating unit of the work shoe or by means of a control and/or regulating unit of the portable machine tool. In this case, safety parameters, such as, for example, a kickback parameter, a maximum torque, a maximum rotational speed, impact energy, a position of a protective cover, and/or a release torque of an overload clutch can be set, for example, by means of the control and/or regulating unit of the work shoe or the control and/or regulating unit of the portable machine tool. The safety parameters in this case are preferably dependent upon a type of machine tool. Therefore, a comfortable setting of safety functions can be advantageously made possible. In addition, a high level of safety of a shoe wearer during an operation of a portable machine tool can be advantageously achieved.

The work shoe according to the disclosure and/or the safety system according to the disclosure should not be limited, in this case, to the above-described application and embodiment. In particular, the work shoe according to the disclosure and/or the safety system according to the disclosure can have a number of individual elements, components, and units which deviates from a number mentioned herein, in order to operate in a manner described herein. In addition, in respect of the value ranges indicated in this disclosure, values lying with the stated limits should also be considered to be disclosed and to be usable in any manner.

BRIEF DESCRIPTION OF THE DRAWINGS

Further advantages result from the following description of the drawing. The drawing shows a representation of one exemplary embodiment of the disclosure. The drawing, the description, and the claims contain numerous features in combination. A person skilled in the art will advantageously also consider the features individually and group them into further reasonable combinations.

In the drawings.

DETAILED DESCRIPTION

Figure 1:
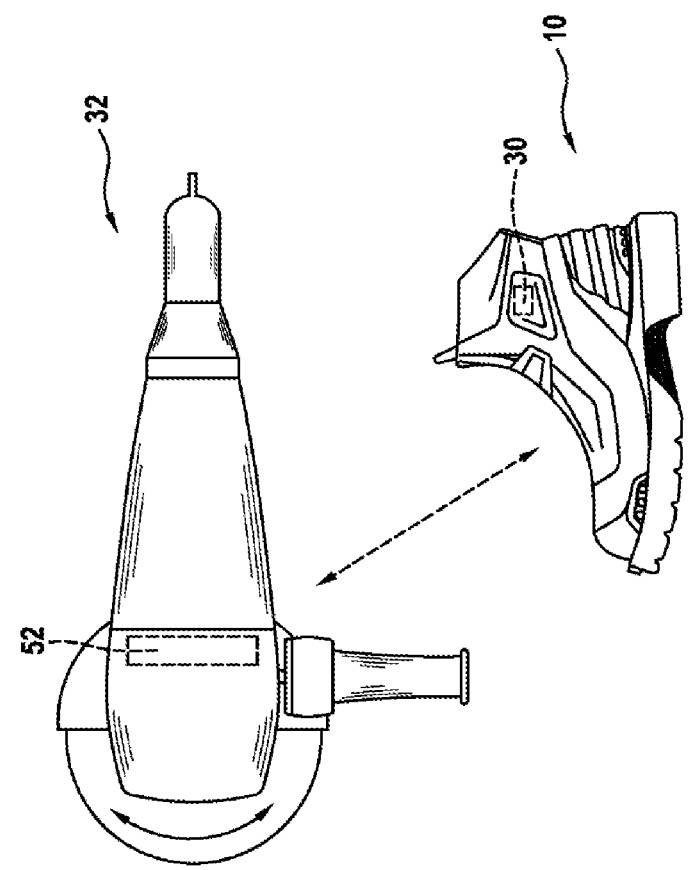
FIG. 1 shows a schematic representation of a safety system according to the disclosure comprising at least one work shoe and at least one external unit.

FIG. 1 shows a safety system 50 comprising at least one work shoe 10 and at least one external unit 32, with which the work shoe 10 communicates at least by means of at least one communication unit 30 of the work shoe 10 in order to exchange electronic data. In all, the safety system 50 comprises at least two work shoes 10 which, together, form a pair (only one work shoe 10 is represented in FIG. 1). It is also conceivable, however, that only one work shoe 10 of a work shoe pair is designed for including a communication unit 30 and/or further units in order to detect characteristic variables and/or for exchanging electronic data with the external unit 32. The external unit 32 is designed as a portable machine tool. It is also conceivable, however, that the external unit 32 has another embodiment which appears reasonable to a person skilled in the art.

The external unit 32 designed as a portable machine tool is designed as an angle grinder, by way of example, in FIG. 1. It is also conceivable, however, that the external unit 32 designed as a portable machine tool is designed as another machine tool which appears reasonable to a person skilled in the art, such as, for example, a circular saw, a drilling machine, an impact drill, a rotary hammer and/or a chisel hammer, or the like. For the purpose of communicating with the communication unit 30 of the work shoe 10, the external unit 32 includes at least one counter-communication unit 52 which is designed to correspond to the communication unit 30 of the work shoe 10 at least in respect of a data transmission method. Furthermore, the external unit 32 can comprise at least one sensor unit which is provided for detecting at least one characteristic variable, wherein the detected characteristic variable can be transmitted to the work shoe 10, by means of an interaction of the counter-communication unit 52 and the communication unit 30, for further processing and/or storage.

Figure 2:
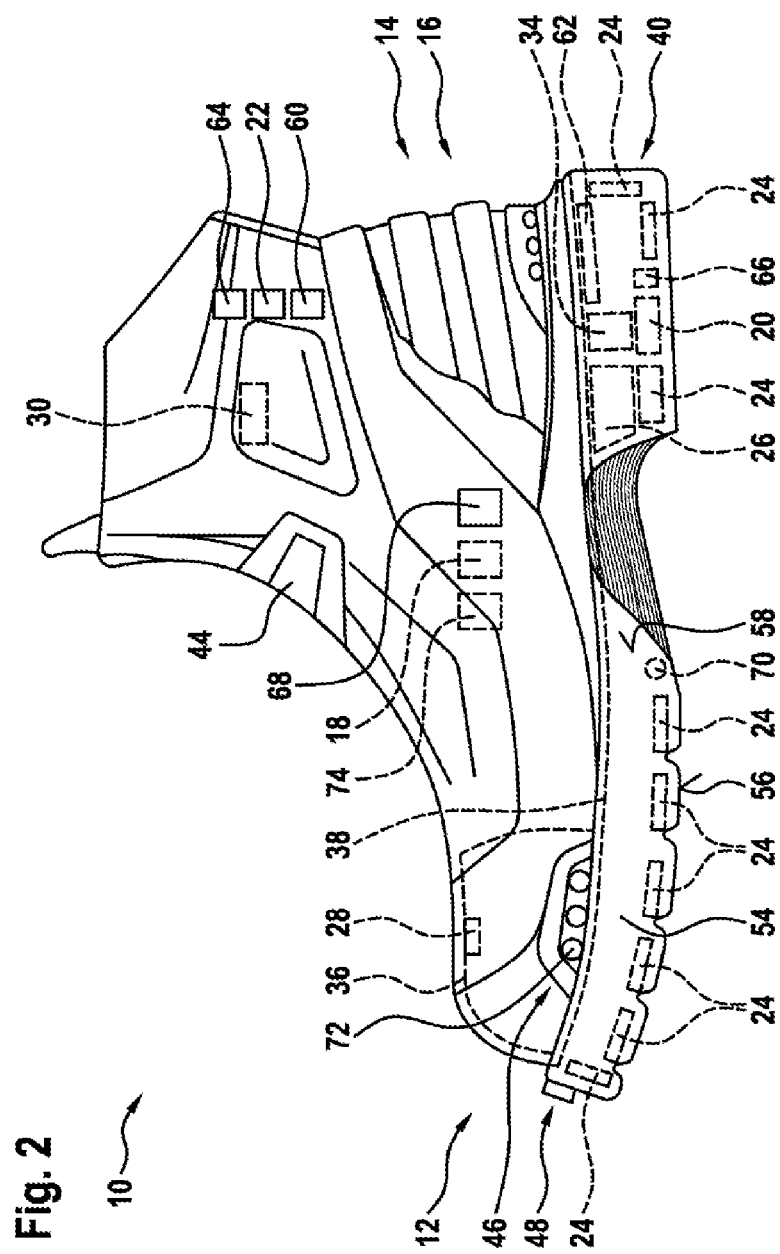
FIG. 2 shows a detailed view of a schematic representation of the work shoe according to the disclosure.

FIG. 2 shows a detailed view of the work shoe 10. The work shoe 10 is designed as a safety shoe in this case. The work shoe 10 therefore includes at least one passive protective unit 12 which is provided for passively protecting a shoe wearer (not shown here in greater detail) at least against mechanical and/or electrical loads. In this case, the passive protective unit 12 includes at least one protective element 36 designed as a safety toecap element. The protective element 36 designed as a safety toecap element is situated in a toe region of the work shoe 10 in a manner which is already known to a person skilled in the art. In this case, the protective element 36 designed as a safety toecap element is preferably made from a metallic material. It is also conceivable, however, that the protective element 36 designed as a safety toecap element is made from a plastic. Furthermore, the passive protective unit 12 includes at least one protective element 38 designed as an anti-penetration element. The protective element 38 designed as an anti-penetration element is situated in or on a sole 54 of the work shoe 10 in a manner which is already known to a person skilled in the art. In this case, the protective element 38 designed as an anti-penetration element is preferably made from a metallic material. It is also conceivable, however, that the protective element 38 designed as an anti-penetration element is made from a plastic or from a woven fabric structure, such as, for example, from a Kevlar structure.

Furthermore, the work shoe 10 includes at least one active protective unit 14 which comprises at least one sensor unit 16 which is provided for detecting at least one characteristic variable at least for enabling a safety function and/or a comfort function. The sensor unit 16 is provided at least for detecting at least one person-related characteristic variable and/or at least one environmental characteristic variable. In this case, the sensor unit 16 includes at least one temperature sensor element 18 which is provided for detecting at least one temperature characteristic variable. The temperature sensor element 18 is designed as a body temperature sensor element which is provided for detecting a body temperature of a shoe wearer. For this purpose, the temperature sensor element 18 is situated on an inner region of the work shoe 10, in particular on an inner region which faces a shoe wearer and rests directly against a shoe wearer when the work shoe 10 is worn. In this case, the temperature sensor element 18, which is designed as a body temperature sensor element, can be designed as a contact sensor element which detects a temperature characteristic variable as a result of a direct contact, or the temperature sensor element 18, which is designed as a body temperature sensor element, can be designed as a contactless sensor element which detects a temperature characteristic variable by means of electromagnetic waves, such as, for example, infrared waves.

In addition, the sensor unit 16 comprises at least one further temperature sensor element 20 which is provided for detecting at least one further temperature characteristic variable. In this case, the further temperature sensor element 20 is designed as an underlying-surface temperature sensor element which is provided for detecting an underlying-surface temperature of an underlying surface (not shown here in greater detail), on which the work shoe 10 is situated. For this purpose, the further temperature sensor element 20 is situated on the sole 54 of the work shoe 10. The further temperature sensor element 20 can be designed as a contact sensor element or as a contactless sensor element. In this case, the further temperature sensor element 20 can be situated on a sole surface 56 of the sole 54 facing an underlying surface, or the further temperature sensor element 20 can be situated on a lateral surface 58 of the sole 54 extending transversely to the sole surface 56, wherein the further temperature sensor element 20 has a detection angle which is oriented in the direction of an underlying surface.

In addition, the sensor unit 16 includes at least one additional temperature sensor element 22 which is provided for detecting at least one additional temperature characteristic variable. In this case, the additional temperature sensor element 22 is designed as an ambient temperature sensor element which is provided for detecting an ambient temperature, in particular an ambient air temperature, of surroundings of the work shoe 10. For this purpose, the additional temperature sensor element 22 is situated on an outer side of the work shoe 10. In this case, the additional temperature sensor element 22 can be integrated directly into a material of an upper material of the work shoe 10.

In addition, the sensor unit 16 includes at least one electronic sensor element 66 which is provided for detecting at least one electrical characteristic variable. The electronic sensor element 66 is designed as a capacitive sensor element. In this case, the electronic sensor element 66 is provided for detecting an electrical characteristic variable in the form of resistance. For this purpose, the electronic sensor element 66 is situated on the sole 54 of the work shoe 10. The electronic sensor element 66 is therefore provided for detecting a conductivity of an underlying surface. It is also conceivable, however, that the electronic sensor element 66 has another embodiment which appears reasonable to a person skilled in the art or that the electronic sensor element 66 is situated at another position on the work shoe 10 which appears reasonable to a person skilled in the art. In addition, it is feasible that the sensor unit 16 comprises a number of electronic sensor elements 66 which deviates from a single electronic sensor element 66. Furthermore, the sensor unit 16 includes at least one further electronic sensor element 70 which is provided for detecting at least one further electrical characteristic variable. In this case, the electronic sensor element 70 is provided for detecting an electrical characteristic variable in the form of voltage.

The sensor unit 16 also includes at least one gas sensor element 68 which is provided for detecting at least one ambient gas characteristic variable. The gas sensor element 68 is situated on the outer side of the work shoe 10. Therefore, a gas composition of an ambient air can be advantageously evaluated as a result of a detection of at least one ambient gas characteristic variable. Therefore, a shoe wearer can be warned, advantageously, against a hazardous gas composition of an ambient air, such as, for example, a gas composition of the ambient air having a high portion of carbon dioxide or carbon monoxide, or a gas composition can be output, in particular by means of an output unit 44 of the work shoe 10.

The sensor unit 16 further includes at least one pressure sensor element 24 which is provided for detecting at least one pressure characteristic variable, in particular a sole-pressure characteristic variable acting onto the sole 54 of the work shoe 10 by a shoe wearer. Preferably, the sensor unit 16 includes a plurality of pressure sensor elements 24 which are situated on the sole 54 of the work shoe 10. The pressure sensor elements 24 are situated so as to be distributed in areas on the sole 54 of the work shoe 10. In this case, some of the pressure sensor elements 24 are situated in an anterior foot region of the sole 54 of the work shoe 10. Some of the pressure sensor elements 24 are situated in a central foot region of the sole 54 of the work shoe 10. In this case, some of the pressure sensor elements 24 are situated in a heel region of the sole 54 of the work shoe 10. Preferably, pressure sensor elements 24 situated in the anterior foot region, in the central foot region, and in the heel region of the sole 54 of the work shoe 10 can be evaluated independently of each other. It is also conceivable, however, that the pressure sensor elements 24 are situated so as to be evenly distributed over an entire region of the sole 54 of the work shoe 10. In this case, it is feasible that the pressure sensor elements 24 are situated on the sole 54 of the work shoe 10 on a side of the protective element 38 of the passive protective unit 12 designed as an anti-penetration element, which side faces away from the sole surface 56, or that the pressure sensor elements 24 are integrated into the sole 54 of the work shoe 10. Furthermore, it is feasible that the pressure sensor elements 24 form a shoe insert which can be removed from the work shoe 10, which pressure sensor elements can be connected to the work shoe 10 by means of a wireless or a cable-bound connection.

The work shoe 10 also includes at least one evaluation unit 26 which is provided, at least, for evaluating the detected pressure characteristic variable in order to detect a sole-load distribution. In this case, the evaluation unit 26 is provided, in particular, for evaluating all characteristic variables, by means of the sensor unit 16, for the purpose of further processing. In addition, the evaluation unit 26 is provided for evaluating pressure characteristic variables of both work shoes 10 of the work shoe pair or for evaluating only the pressure characteristic variable of a single work shoe 10 of the work shoe pair. In this case, it is possible to deduce that a shoe wearer is kneeling or is standing on a ladder, that the sole 54 is resting via the entire surface thereof against an underlying surface, that the shoe wearer is standing on the tips of his toes, etc., on the basis of an evaluation of the detected pressure characteristic variable, in particular a sole-pressure characteristic variable acting onto the sole 54 of the work shoe 10 by a shoe wearer. It is therefore possible to deduce an orientation of the work shoe 10 and/or a load type of the work shoe 10 on the basis of a physical stance of a shoe wearer, advantageously by means of an evaluation of the detected pressure characteristic variable, in particular a sole-pressure characteristic variable acting onto the sole 54 of the work shoe 10 by a shoe wearer.

Furthermore, the sensor unit 16 includes at least one further pressure sensor element 60 which is provided for detecting a pressure characteristic variable in the form of an ambient-pressure characteristic variable. Therefore, a height at which the work shoe 10 is located can be advantageously deduced, for example, by means of the evaluation unit 26. In this case, the further pressure sensor element 60 is situated on the outer side of the work shoe 10. The sensor unit 16 can also include further pressure sensor elements 24 which appear reasonable to a person skilled in the art and which are provided for detecting at least one pressure characteristic variable.

Furthermore, the sensor unit 16 includes at least one location-determining sensor element 28 which is provided for detecting at least one position characteristic variable, in particular at least one global position characteristic variable and/or at least one relative work-area position characteristic variable. For this purpose, the sensor unit 16 includes at least one location-determining sensor element 28 which is designed as a global location-determining sensor element and is provided for detecting a global position characteristic variable. The location-determining sensor element 28 designed as a global location-determining sensor element is preferably designed as a GPS location-determining element. In addition, the sensor unit 16 includes at least one work area location-determining sensor element 64 which is provided for detecting at least one relative work-area position characteristic variable. The work area location-determining sensor element 64 is preferably provided for detecting at least one orientation, such as, for example, a horizontal or a vertical orientation, of the work shoe 10. The work area location-determining sensor element 64 is therefore designed at least as a position sensor element, such as, for example, a multidirectional acceleration sensor element, a gyro sensor element, a rotation rate sensor element, etc. However, it is also conceivable that, in addition or alternatively to a detection of a work area position characteristic variable, the sensor unit 16 detects at least one relative work area position characteristic variable via a transit time measurement of signals from the communication unit 30 by means of the work area location-determining sensor element 64. The spatial position in which a shoe wearer is situated can therefore be detected, for example, as a result of an evaluation of the position characteristic variable by means of the evaluation unit 26. As a result, it can be advantageously deduced whether a shoe wearer is in a dangerous situation, in particular if an acceleration sensor element 74 of the sensor unit 16 does not detect movement and a shoe wearer does not change position over a certain period of time. Furthermore, an acceleration characteristic variable in the form of muscular twitching, for example, can be detected by means of the acceleration sensor element 74, which variable can be utilized in order to detect a dangerous situation of a shoe wearer, such as, for example, a detection of a dizzy spell, a detection of a safe state, such as, for example, a safe state on a ladder, on the tips of toes, etc., or the like. The sensor unit 16 therefore includes at least the acceleration sensor element 74 which is provided for detecting at least one acceleration characteristic variable which can be utilized at least in order to evaluate a safe state of a shoe wearer. In this case, the detected acceleration characteristic variable should be evaluated at least in order to detect a safe state of a shoe wearer by means of the evaluation unit 26. In addition, the sensor unit 16 can include further sensor elements which appear reasonable to a person skilled in the art, such as, for example, a moisture sensor element, a pH value sensor element, a pulse sensor element, a blood pressure sensor element, etc., which are provided for detecting at least one person-related characteristic variable and/or at least one environmental characteristic variable, which can be evaluated by means of the evaluating unit 26.

Figure 3:
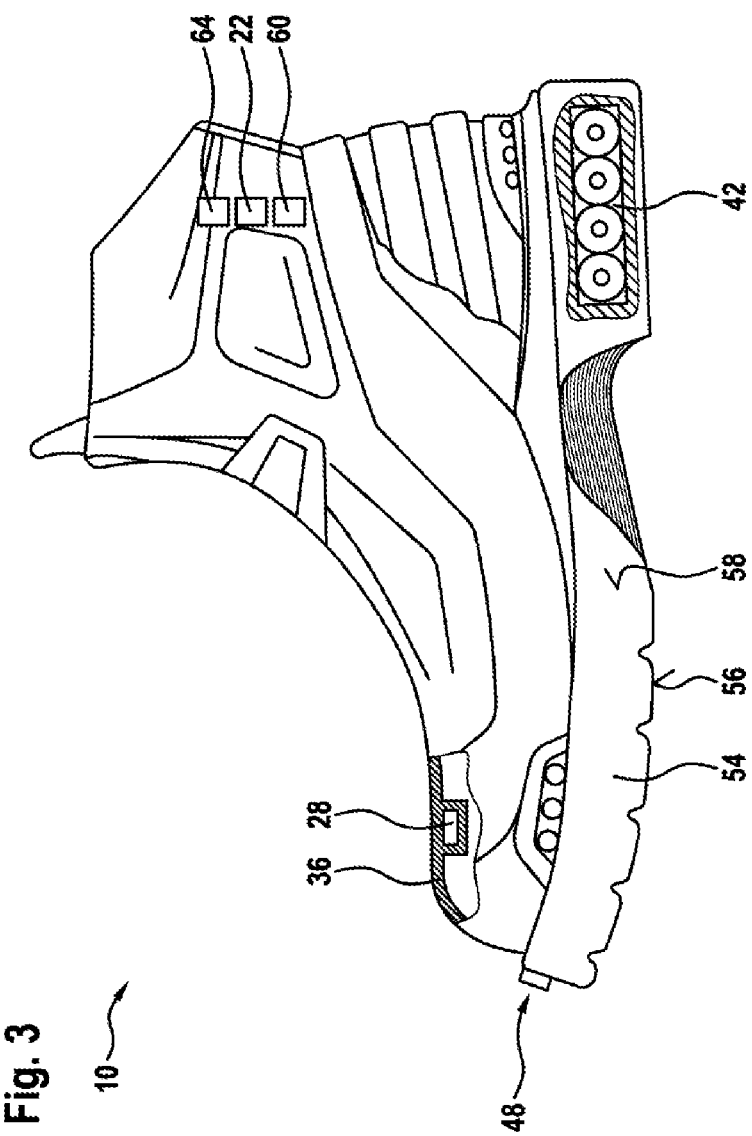
FIG. 3 shows a partial sectional view of a schematic representation of the work shoe according to the disclosure.

The sensor unit 16 is preferably at least partially situated in or on one of the passive protective elements 36, 38 of the passive protective unit 12. In this case, it is conceivable that at least one sensor element, such as, for example, the location-determining sensor element designed as a global location-determining sensor element, of the sensor unit 16 is situated in the protective element 36 designed as a safety toecap element (FIG. 3). The protective element 36 designed as a safety toecap element can therefore form a housing of the sensor unit 16. It is also conceivable that further units of the work shoe 10 are situated at least partially in or at the passive protective unit 12, such as, for example, a power supply unit 40 of the work shoe 10, an energy accumulator unit 42 of the work shoe 10, etc. It is also conceivable that the sensor unit 16, in an alternative embodiment, is situated at least partially on the protective element 38 designed as an anti-penetration element, wherein, in an embodiment made from a metallic material, the protective element 38 designed as an anti-penetration element can be provided as a heat sink for the sensor unit 16.

The work shoe 10 includes at least one communication unit 30 which is provided for communicating with at least the external unit 32 in order to exchange electronic data. In this case, it is conceivable that the electronic data are in the form of raw data from the sensor unit 16 or that the electronic data are data which have already been evaluated by means of the evaluation unit 26. The communication unit 30 is provided for automatically checking, while the work shoe 10 is being worn, whether a suitable external unit 32 is within communication range. After a detection and a connection to a suitable external unit 32, an exchange of electronic data begins. In the case of the external unit 32 represented in FIG. 1, which is designed as a portable machine tool, in particular as an angle grinder, it is conceivable that work on a ladder is detected on the basis of an evaluation of at least one person-related characteristic variable detected by means of the sensor unit 16 and/or on the basis of an evaluation of an environmental characteristic variable by means of the evaluation unit 26, and that a kickback setting of the external unit 32 designed as a portable machine tool is at least partially automatically adjustable as the result of communication between the external unit 32 designed as a portable machine tool the work shoe 10. Therefore, a risk of injury to a shoe wearer in the event of a sudden jamming of a insert tool can be advantageously minimized and, therefore, a fall from the ladder can be advantageously prevented.

In addition, a free fall of a shoe wearer from a ladder can be detected by means of the evaluation unit 26, for example, as a result of an evaluation of at least one person-related characteristic variable and/or environmental characteristic variable, which are/is detected by means of the sensor unit 16. For this purpose, an acceleration characteristic variable detected by means of the acceleration sensor element 74 of the sensor unit 16 can be evaluated by the evaluation unit 26. By means of the communication unit 30, a detection of the free fall can therefore be forwarded to external units 32, wherein, for example, an external unit 32 designed as a portable machine tool can be automatically switched off in order to reduce putting a shoe wearer at risk and to avoid possible injury. Furthermore, an impact of a shoe wearer after a fall can be detected by means of the evaluation unit 26, for example, as a result of an evaluation of at least one person-related characteristic variable and/or environmental characteristic variable, which are/is detected by means of the sensor unit 16. Detected pressure characteristic variables and position characteristic variables of the sensor unit 16 can be evaluated for this purpose. It is therefore advantageously possible to detect whether a shoe wearer is still standing or lying down or if he may have become injured in the fall. In addition, the information can be made more precise, e.g., whether unconciousness is present. Vital characteristic variables, such as, for example, a pulse characteristic variable, of the sensor unit 16 can be evaluated for this purpose. An accident and/or danger notification to an external unit designed as a control center (not shown here in greater detail) can take place by means of the communication unit 30 or can be dispatched to an external unit as an accident reporting center (not shown here in greater detail). If communication by means of the communication unit 30 has been deactivated and/or is impossible, the electronic data can be stored in a memory unit (not shown here in greater detail) of the work shoe 10. Therefore, the memory unit can be advantageously utilized as a data recorder/accident recorder which stores, e.g., the data for a defined unit of time and continuously overwrites said data.

In addition, the work shoe 10 includes at least one control and/or regulating unit 34 which is provided for adapting at least one work shoe parameter, in particular a work shoe comfort parameter and/or a work shoe safety parameter, depending on the at least one detected, person-related characteristic variable and/or on the at least one detected environmental characteristic variable. In this case, it is conceivable that, for example, a heating function of a heating unit (not shown here in greater detail) or a cooling function of a cooling unit (not shown here in greater detail) of the work shoe 10 can be adapted, by means of the control and/or regulating unit 34, depending on the at least one detected, person-related characteristic variable and/or on the at least one detected environmental characteristic variable. Furthermore, it is also conceivable that an adaptation of at least one work shoe parameter, in particular a work shoe comfort parameter and/or a work shoe safety parameter takes place by means of the control and/or regulating unit 34 as a result of an exchange of electronic data by means of the communication unit 30. As a result, for example, a heating function of a heating unit (not shown here in greater detail) or a cooling function of a cooling unit (not shown here in greater detail) of the work shoe 10 could be controlled and/or regulated by means of communication with a smartphone.

Furthermore, the control and/or regulating unit 34 is provided for accessing a central database by means of the communication unit 30, in which at least one safety and/or operating-area rule are/is stored, which can be utilized at least for adapting at least one work shoe parameter and/or for outputting safety information by means of the output unit 44 of the work shoe 10. Therefore, for example, a shoe wearer can be informed by means of the output unit 44 as to which safety and/or operating-area rules apply and must be complied with in an area in which he is situated.

In addition, the work shoe 10 includes at least the power supply unit 40 and/or the energy accumulator unit 42 (FIGS. 2 and 3) for supplying energy to the active protective unit 14. In this case, the power supply unit is designed as a piezo energy supply unit which comprises at least one piezo element 62. In this case, the piezo element 62 is situated on the sole 54 of the work shoe 10. In an embodiment of the work shoe 10 which is not represented here in greater detail, the protective element 38 designed as an anti-penetration element has a two-layer design, wherein the piezo element 62 is situated between two layers of the protective element 38 designed as an anti-penetration element. In this case, the power supply unit 40 preferably includes a plurality of piezo elements 62 which are situated so as to be distributed between the two layers of the protective element 38 designed as an anti-penetration element. Alternatively, however, the power supply unit 40 can also be designed as an inductive power supply unit or as a cable power supply unit. In addition, the power supply unit 40 is connected to the energy accumulator unit 42 in a manner which is already known to a person skilled in the art, by means of a power supply line (not shown here in greater detail). The energy accumulator unit 42 is designed as a rechargeable battery unit in this case. In this case, the energy accumulator unit 42 is situated in the sole 54 of the work shoe 10 (FIG. 3). In this case, the energy accumulator unit 42 can be situated in the sole 54 of the work shoe 10 so as to be exchangeable. In addition, it is conceivable that the energy accumulator unit 42 is designed as an external energy accumulator unit which is connectable to the work shoe 10 by means of a power supply line and, for example, can be situated on a belt worn by a shoe wearer. The power supply unit 40 and/or the energy accumulator unit 42 include at least one back-up unit which is provided for enabling basic function of the active protective unit 14 in an emergency operating mode, such as, for example, outputting a message by means of the output unit 44 in the event of a low energy content of the energy accumulator unit 42, etc.

The work shoe 10 includes at least the output unit 44 for outputting information at least depending on the at least one detected person-related characteristic variable and/or on the at least one detected environmental characteristic variable and/or depending on information transmitted by means of a communication unit 30. Therefore, different temperature characteristic variables can be displayed, for example, by means of the output unit 44, wherein the output unit 44 in this case includes at least one output element designed as a display and/or one output element designed as a lighting element, in particular as an LED. For example, a ground temperature can be displayed in shades of color, wherein, in particular, blue represents a temperature of less than 50° C., green represents a temperature of 20° C., and red represents a temperature of more than 40° C. By means of the output unit 44, a warning message can therefore be advantageously output in the event of an imminent danger (voltage on the underlying surface, caustic fluid on the underlying surface, the underlying-surface temperature is too high, risk of glare ice, or the like). In addition, optical feedback as to whether the communication unit 30 is connected to an external unit 32 can be sent to a shoe wearer by means of the output unit 44. A shoe wearer can therefore advantageously determine whether a communication connection has been reliably established.

In addition, it is conceivable in this case that the type of external unit to which the communication unit 30 is connected and with which it communicates is additionally displayed to a shoe wearer by the output unit 44.

Furthermore, the work shoe 10 includes at least one lighting unit 46 for illuminating a work area. The lighting unit 46 includes at least one lighting element 72 which is situated on a toe region of the work shoe 10 and is provided for illuminating a work area. The lighting element 72 is designed as an LED. The lighting unit 46 can have a number of lighting elements 72 which deviates from a single lighting element 72, which are situated on a work shoe 10 and are provided for lighting a work area. In this case, it is conceivable that the lighting unit 46 can be manually controlled by a shoe wearer or that the lighting unit 46 can be controlled and/or regulated by means of the control and/or regulating unit 34, in particular at least depending on at least one light characteristic variable detected by means of a light sensor element (not shown here in greater detail) of the sensor unit 16.

In addition, the work shoe 10 includes at least one projection unit 48 which is provided for projecting at least one piece of information onto an underlying surface. By means of the projection unit 48, persons advantageously located in the surroundings of a shoe wearer can be advantageously informed about a danger or can be informed about a state of a shoe wearer in an emergency situation. The projection unit 48 is preferably designed as a beamer unit. In this case, the projection unit 48 can be designed as a laser beamer unit or as another projection unit which appears reasonable to a person skilled in the art.

The invention claimed is:

1. A work shoe, comprising:
    at least one passive protection unit configured to protect passively a shoe wearer at least against mechanical and/or electrical loads, and
    at least one active protection unit including at least one sensor unit configured to detect at least one characteristic variable at least in order to enable a protective function and/or a comfort function, the at least one sensor unit further configured to detect at least one person-related characteristic variable and/or at least one environmental characteristic variable,
    wherein the at least one sensor unit comprises at least one location-determining sensor element configured to detect at least one position characteristic variable,
    wherein the at least one passive protection unit includes a safety toecap element formed of a metal or plastic material, and
    wherein the location-determining sensor element is situated in the safety toecap element such that the safety toecap element forms a housing for the location-determining sensor element.

2. The work shoe as claimed in claim 1, wherein the at least one sensor unit includes at least one acceleration sensor element configured to detect at least one acceleration characteristic variable for utilization at least for evaluating a safe state of the shoe wearer.

3. The work shoe as claimed in claim 2, wherein the at least one sensor unit includes at least one pressure sensor element configured to detect at least one pressure characteristic variable.

4. The work shoe as claimed in claim 3, further comprising:
    at least one evaluation unit configured to evaluate the detected acceleration characteristic variable in order to detect a safe state of the shoe wearer and/or to evaluate the detected pressure characteristic variable in order to detect a sole load distribution.

5. The work shoe as claimed in claim 3, wherein the at least one pressure characteristic variable includes a sole-pressure characteristic variable acting onto a sole of the work shoe by the shoe wearer.

6. The work shoe as claimed in claim 1, wherein the at least one sensor unit includes at least one temperature sensor element configured to detect at least one temperature characteristic variable.

7. The work shoe as claimed in claim 6, wherein the at least one temperature characteristic variable includes a body temperature, an underlying-surface temperature, and/or an ambient temperature.

8. The work shoe as claimed in claim 1, further comprising:
    at least one communication unit configured to communicate with at least one external unit to exchange electronic data.

9. The work shoe as claimed in claim 8, further comprising:
    at least one control and/or regulating unit configured to adapt at least one work shoe parameter depending on the at least one detected, person-related characteristic variable and/or on the at least one detected environmental characteristic variable.

10. The work shoe as claimed in claim 9, wherein the control and/or regulating unit is further configured to access a central database with the communication unit, in which at least one safety and/or operating-area rule are/is stored, for utilization at least for adapting at least one work shoe parameter and/or for outputting safety information with the output unit.

11. The work shoe as claimed in claim 9, wherein the at least one work shoe parameter includes a work shoe comfort parameter and/or a work shoe safety parameter.

12. The work shoe as claimed in claim 8, further comprising:
    at least one output unit configured to output information at least depending on the at least one detected person-related characteristic variable and/or on the at least one detected environmental characteristic variable and/or depending on information transmitted by the at least one communication unit.

13. The work shoe as claimed in claim 1, further comprising:
    at least one power supply unit and/or one energy accumulator unit configured at least to supply power to the active protective unit.

14. The work shoe as claimed in claim 1, further comprising:
    at least one lighting unit configured to illuminate a work area.

15. The work shoe as claimed in claim 1, further comprising:
    at least one projection unit configured to project at least one piece of information onto an underlying surface.

16. The work shoe as claimed in claim 1, wherein the at least one position characteristic variable includes at least one global position characteristic variable and/or at least one relative work-area position characteristic variable.

17. A safety system comprising:
    at least one work shoe including (i) at least one passive protection unit configured to protect passively a shoe wearer at least against mechanical and/or electrical loads, (ii) at least one active protection unit including at least one sensor unit configured to detect at least one characteristic variable at least in order to enable a protective function and/or a comfort function, the at least one sensor unit further configured to detect at least one person-related characteristic variable and/or at least one environmental characteristic variable, and (iii) at least one communication unit; and
    at least one external unit with which the at least one work shoe is configured to communicate using the at least one communication unit in order to exchange electronic data, wherein the at least one sensor unit comprises at least one location-determining sensor element configured to detect at least one position characteristic variable, wherein the at least one passive protection unit includes a safety toecap element formed of a metal or plastic material, and wherein the location-determining sensor element is situated in the safety toecap element such that the safety toecap element forms a housing for the location-determining sensor element.

18. The safety system as claimed in claim 17, wherein the at least one external unit is configured as a portable machine tool.

\* \* \* \* \*